US010006876B2

(12) United States Patent
Ghandi et al.

(10) Patent No.: US 10,006,876 B2
(45) Date of Patent: Jun. 26, 2018

(54) NANOSTRUCTURED MICROBIAL SENSORS

(71) Applicant: ChemGreen Innovation Inc., Sackville (CA)

(72) Inventors: Khashayar Ghandi, Sackville (CA); Zahid Mahimwalla, Sackville (CA); Tan Yang, Sackville (CA); Cody Landry, Sackville (CA)

(73) Assignee: ChemGreen Innovation Inc., Sackville, New Brunswick (CA)

( * ) Notice: Subject to any disclaimer, the term of this patent is extended or adjusted under 35 U.S.C. 154(b) by 592 days.

(21) Appl. No.: 14/531,702

(22) Filed: Nov. 3, 2014

(65) Prior Publication Data

US 2015/0126409 A1 May 7, 2015

Related U.S. Application Data

(60) Provisional application No. 61/898,665, filed on Nov. 1, 2013.

(51) Int. Cl.
| | |
|---|---|
| *G01N 21/64* | (2006.01) |
| *G01N 27/12* | (2006.01) |
| *B82Y 15/00* | (2011.01) |
| *G01N 21/77* | (2006.01) |
| *G01N 27/403* | (2006.01) |
| *G01N 33/543* | (2006.01) |

(52) U.S. Cl.
CPC ............ *G01N 27/127* (2013.01); *B82Y 15/00* (2013.01); *G01N 21/64* (2013.01); *G01N 21/77* (2013.01); *C12Q 2565/607* (2013.01); *G01N 33/54346* (2013.01); *G01N 2021/7786* (2013.01)

(58) Field of Classification Search
CPC .......... G01N 2021/7786; G01N 21/77; G01N 27/127
See application file for complete search history.

(56) References Cited

U.S. PATENT DOCUMENTS

| | | | |
|---|---|---|---|
| 7,889,334 B2 * | 2/2011 | Krause ..................... | B82Y 5/00 356/301 |
| 8,501,414 B2 | 8/2013 | Danzer et al. | |
| 2003/0134433 A1 * | 7/2003 | Gabriel .................. | B82Y 30/00 436/518 |

(Continued)

FOREIGN PATENT DOCUMENTS

EP       1712614     10/2006

OTHER PUBLICATIONS

Tauxe, R.; Kruse, H.; Hedberg, C.; Potter, M.; Madden, J.; Wachsmuth, K. Microbial Hazards and Emerging Issues Associated with Produce: A Preliminary Report to the National Advisory Committee on Microbiologic Criteria for Foods. J. Food Prot. 60, 1400-1408, 1997.

(Continued)

*Primary Examiner* — Jennifer Wecker
(74) *Attorney, Agent, or Firm* — Bereskin & Parr LLP/S.E.N.C.R.L., s.r.l.; Michael Fenwick

(57) ABSTRACT

The present invention relates to the detection of microbial organisms using non-toxic nanostructured sensors that change their physical or chemical properties upon detecting these microbial organisms. These sensors allow an unskilled person to rapidly detect the presence of microbial contamination.

19 Claims, 5 Drawing Sheets

(56) References Cited

U.S. PATENT DOCUMENTS

| | | | |
|---|---|---|---|
| 2004/0106203 A1* | 6/2004 | Stasiak | G01N 27/3278 422/82.01 |
| 2005/0169798 A1* | 8/2005 | Bradley | B82Y 15/00 422/400 |
| 2009/0202985 A1* | 8/2009 | Gulak | C12Q 1/18 435/5 |
| 2010/0112546 A1* | 5/2010 | Lieber | A61B 5/14546 435/5 |
| 2011/0091510 A1* | 4/2011 | Lele | B82Y 30/00 424/400 |
| 2012/0183452 A1* | 7/2012 | Schalkhammer | G01N 21/78 422/426 |
| 2013/0084586 A1 | 4/2013 | Hegde et al. | |
| 2013/0252843 A1* | 9/2013 | Yan | A61K 49/0043 506/9 |
| 2014/0106469 A1* | 4/2014 | Wu | G01N 33/54346 436/501 |

OTHER PUBLICATIONS

Wilcock, A.; Pun, M.; Khanona, J.; Aung, M. Consumer attitudes, knowledge and behaviour: a review of food safety issues. Trends Food Sci. Technol. 2004, 15, 56-66.

Alivisatos, P. The use of nanocrystals in biological detection. Nat. Biotechnol. 2004, 22, 47-52.

Sanvicens, N.; Pastells, C.; Pascual, N.; Marco, M.-P. Nanoparticle-based biosensors for detection of pathogenic bacteria. TrAC Trends Anal. Chem. 2009, 28, 1243-1252.

Barth, S.; Hernandez-Ramirez, F.; Holmes, J. D.; Romano-Rodriguez, A. Synthesis and applications of one-dimensional semiconductors. Prog. Mater. Sci. 2010, 55, 563-627.

Bancquart, S.; Vanhove, C.; Pouilloux, Y.; Barrault, J. Glycerol transesterification with methyl stearate over solid basic catalysts. Appl. Catal. A Gen. 2001, 218, 1-11.

Liu, F.; Zhang, Y. Controllable growth of "multi-level tower" ZnO for biodiesel production. Ceram. Int. 2011, 37, 3193-3202.

Zeng, J. H.; Jin, B. Bin; Wang, Y. F. Facet enhanced photocatalytic effect with uniform single-crystalline zinc oxide nanodisks. Chem. Phys. Lett. 2009, 472, 90-95.

Baruah, S.; Pal, S. K.; Dutta, J. Nanostructured Zinc Oxide for Water Treatment. Nanosci. Nanotechnology-Asia 2012, 2,90-102.

Lin, Y.-G.; Hsu, Y.-K.; Chen, S.-Y.; Lin, Y.-K.; Chen, L.-C.; Chen, K.-H. Nanostructured Zinc Oxide Nanorods with Copper Nanoparticles as a Microreformation Catalyst. Angew. Chemie Int. Ed. 2009, 48, 7586-7590.

Zhang, Y.; Yu, K.; Jiang, D.; Zhu, Z.; Geng, H.; Luo, L. Zinc oxide nanorod and nanowire for humidity sensor. Appl. Surf. Sci. 2005, 242, 212-217.

Gu, B. X.; Xu, C. X.; Zhu, G. P.; Liu, S. Q.; Chen, L Y.; Wang, M. L.; Zhu, J. J. Layer by Layer Immobilized Horseradish Peroxidase on Zinc Oxide Nanorods for Biosensing. J. Phys. Chem. B 2009, 113, 6553-6557.

Zhang, F.; Wang, X.; Ai, S.; Sun, Z.; Wan, Q.; Zhu, Z.; Xian, Y.; Jin, L.; Yamamoto, K. Immobilization of uricase on ZnO nanorods for a reagentless uric acid biosensor. Anal. Chim. Acta 2004, 519, 155-160.

Bie, L.-J.; Yan, X.-N.; Yin, J.; Duan, Y.-Q.; Yuan, Z.-H. Nanopillar ZnO gas sensor for hydrogen and ethanol. Sensors Actuators B Chem. 2007, 126, 604-608.

Chai, G.; Lupan, O.; Chow, L.; Heinrich, H. Crossed zinc oxide nanorods for ultraviolet radiation detection. Sensors Actuators A Phys. 2009, 150, 184-187.

Lim, C. T. Synthesis, optical properties, and chemical-biological sensing applications of one-dimensional inorganic semiconductor nanowires. Prog. Mater. Sci. 2013, 58, 705-748.

* cited by examiner

NANOSTRUCTURED MICROBIAL SENSORS

This application claims priority to U.S. Provisional Application No. 61/898,665, filed on Nov. 1, 2013, which is hereby incorporated by reference in its entirety.

FIELD OF THE DISCLOSURE

The present invention relates to the detection of microbial organisms using nanostructured sensors that change their physical or chemical properties upon detecting these microbial organisms.

BACKGROUND OF THE DISCLOSURE

The contamination of consumable food products, both for humans and animals including pet food, animal feed, packaged food meals, raw produce, meat and poultry etc. is a major source of economic and commercial damage, emotional and physical distress and is of concern to public health and wellbeing. One common cause of such contamination is from microbial organisms, namely bacteria and fungi, that can cause spoilage, poisoning, and other adverse health effects resulting in serious health conditions and even death for both humans and animals. This, and other cases of microbial infection outbreaks, has created a significant demand for developing technologies to allow a rapid and cost effective technique of detecting the presence of such microbial organisms, without the need of specialized training, throughout the production supply chain, to the consumer.[1,2]

Current microbial detection techniques rely mostly on isolation and culturing of the various microbial samples or the use of immunoassays (fluorescent and radioactive) to detect macromolecules associated with various bacterial species. Enzyme-linked immunosorbent assay (ELISA) is another derivative technique where enzymes are attached to the antibody to produce more detectable products. Other detection techniques utilize mass spectroscopy techniques in combination with gas chromatography, and pyrolysis methods to detect bacterial byproducts. Flow cytometry can also be used for rapid detection, identification and separation of cells. Total luminescence spectroscopy can also detect cells quite rapidly. A number of these techniques, for example, are mentioned by U.S. Pat. No. 7,889,334 B2, U.S. Pat. No. 8,501,414 B2, US Pat. Pub. No. 20130084586, and European Pat. Pub. No. 1712614 A1.

However, these techniques are often costly, labor intensive, require significant training and skills by the operator and can require the use of a laboratory (culturing of bacteria), expensive equipment (mass spectrometers, fluorescence microscopes) and chemicals (fluorescent and or radioactive chemical labels, antibodies etc.) that make their routine implementation for unskilled persons, consumers, and other areas of the supply chain impractical. The techniques also result in the destruction or contamination of the food sample rendering it unfit for further consumption.

Other approaches to detecting bacteria involve the use of nanostructures.[3] More commonly nanoparticles have been used for signal enhancements, as well as bio-sensing and detection systems to identify microorganism specific molecules by the detection of biological binding events of specific ligands, anti-bodies, chemical labels or analytes[4]. This nanostructure approach to bio-sensing is based on attaching a ligand, or a chemical or biological label, to the nanostructures, which upon interacting either chemically or physically with the target molecule(s) will result in changing the electrical or optical properties of the sensor substrate. This can potentially offer several advantages including limited hands-on time, real-time analysis as well as label-free detection methods and devices[4]. Known examples of this approach (which differ significantly when compared to the biological sensing of the present disclosure) include nanostructures of gold, silver[4] and zinc oxide.[5]

Zinc oxide is a popular choice from a materials perspective for the fabrication of nanostructures due to its catalytic, electrical, optoelectronic, and piezoelectric properties.[6-11]

This detection methodology using nanostructures for biological sensing while advantageous, also suffers from limitations. These include the assumption that the presence of certain molecules indicates active microbial presence, specificity to particular species of microbes or molecules, requiring multiple tests to detect more than one microbial species or molecules. The isolation and coating of the ligands onto the nanostructures can be very costly depending on the type of ligand used.

This approach to bio sensing is the current paradigm in the scientific and patent literature, with the assumption that these nanostructures are inadequate for biological sensing without the coating of ligands onto the nanostructure to discern the binding of specific analytes and thus the biological organism.

SUMMARY OF THE DISCLOSURE

The present disclosure relates to a sensor that changes its physical or chemical properties in the presence of microbial organisms, without being coated by any specific antibodies, analytes, ligands or chemical labels etc. These changes are then translated into a format easily understood by the operator via electronic instruments, or optionally discernible changes in the macroscopic optical or physical properties of the sensor. Thus the sensor is simple to operate, potentially more economical to produce and thus more advantageous in its various applications.

In one embodiment of the invention, the sensor is comprised of an array (ordered, partially-ordered or disordered) of nanostructures composed of one or more of the following components: metal, metal oxide, carbon nanostructures (tubes, balls etc.), and ceramic or polymeric components. In one embodiment the sensor is comprised of metal oxide nanostructures that change their electrical properties upon detection of microbial organisms.

Also included in the present disclosure is a means of modifying the structural dimensions, shape and properties of the nanostructures by use of magnetic and gravity fields.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The disclosure will now be described in greater detail with reference to the following drawings in which.

DETAILED DESCRIPTION OF THE DISCLOSURE

(I) Definitions

Figure 1:
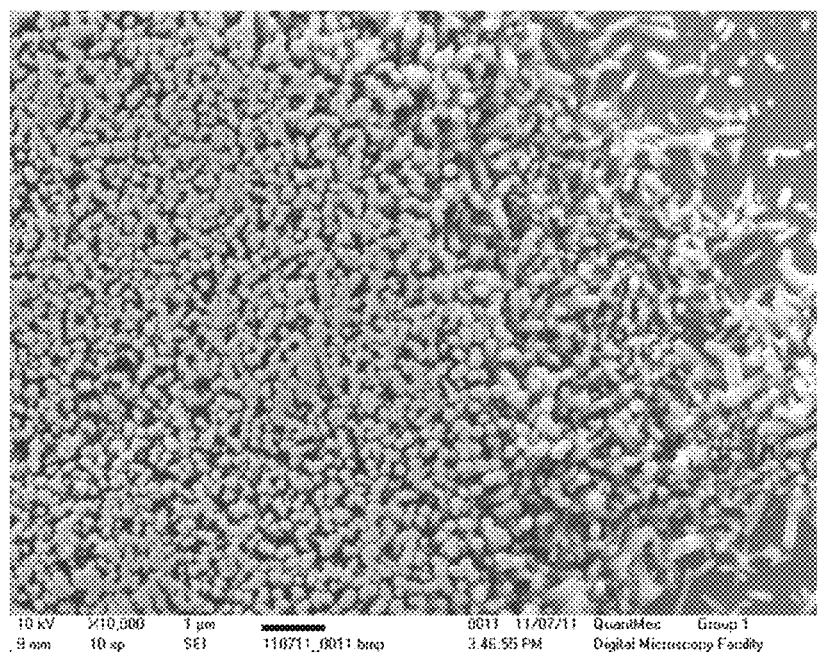
FIG. 1. SEM image of vertically aligned, "gravity assisted", ZnO nanoparticles shown with a 1 μm scale bar. Collapse on right side demonstrates the edge of the doped area. Sample had an initial annealing temperature of 300° C.

The term "consumable food product(s)" as used herein refers to substances, organic matter and other materials both natural and synthetic that are deemed fit for human or animal consumption. Thus this includes animal feed, pet food, approved food additives or food substances, and any food products deemed fit for human consumption, including manufactured, frozen and processed foods, as well as food prepared at catering establishments, restaurants, grocery stores, home kitchens etc.

The term "microbial organisms" as used herein refers to various bacteria and fungi that are responsible for adverse health effects in humans, animals or both, as well as bacteria and fungi that are responsible for the degradation of food such that it is rendered unfit for consumption (spoilage) by its intended consumer.

The term "nanostructure" as used herein refers to the presence of regular or irregular shaped material and objects with at least one dimension on the nanometer scale having a size between 1 and 1000 nm.

The term "nanostructured shapes" as used herein refers to the presence of regular or irregular shaped material and objects with at least one dimension on the nanometer scale having a size between 1 and 1000 nm. Examples of such nanostructured shapes include but are not limited to cubes, spheres, rods, sheets, ellipses, tubes, rings, pillars, ellipsoids, flower-shaped structures, screwdriver shaped structures etc. including combinations of two or more shapes.

The term "microbial sensors" as used herein refers to a sensor capable of changing its physical or chemical properties when it detects the presence of a microbial organism. These changes in the physical or chemical properties of the sensor are detectable, and result in a signal that is optionally visual, tactile, or interpreted by an electronic instrument for the user.

The term "electrical properties" as used herein refers to the electrical properties of materials including its dielectric properties, its electrical conductivity and resistivity, dielectric strength, permeability, permittivity and piezoelectric properties.

(II) Detailed Description

The present disclosure relates to a non-toxic, nanostructured sensor free of any coatings by specific antibodies, analytes, ligands or chemical labels etc. which when in contact with consumable food products or consumable food product packaging materials can detect the presence of microbial organisms. Such nanostructured sensors can be comprised of various nanostructured shapes including but not limited to nanocubes, nanoparticles, nanorods, nanowires, nanobelts, nanotubes, nanoflowers, nanoscrewdrivers etc. or as a combination of multiple nanostructured shapes.

The nanostructured sensor is synthesized with various synthetic methodologies known to one skilled in the art with a modification of the procedure to expose the growing structures to gravity and magnetic fields individually or in combination to obtain the desired dimensions and shape of the nanostructures.

In one embodiment of the invention the nanostructured sensor is comprised of an array (ordered, partially-ordered or disordered) of nanostructures that change their physical or chemical properties including but not limited to optical, electrical properties, opto-electronic, piezoelectric, chemical or catalytic properties when it detects microbial organisms. Such changes in physical or chemical properties are then converted into a format easily read by an operator via electronic instruments, visually or physically detectable changes (examples include color, physical degradation of the sensor), or a combination of the two.

In another embodiment of the invention the nanostructured sensor is comprised of an array (ordered, partially-ordered or disordered) of nanostructures composed of one or more of the following components metal, metal oxide, carbon nanostructures (tubes, balls etc.), ceramic or polymeric components. These arrays change their physical or chemical properties including but not limited to optical, electrical properties, opto-electronic, piezoelectric, chemical or catalytic properties when it detects microbial organisms. Such changes in physical or chemical properties are then converted into a format easily read by an operator via electronic instruments, visually or physically detectable changes, or a combination of the two.

In another embodiment of the invention the nanostructured sensor is comprised of an array (ordered, partially-ordered or disordered) of metal oxide nanostructures that change their physical or chemical properties including but not limited to optical, electrical properties, opto-electronic, piezoelectric, chemical or catalytic properties when it detects microbial organisms. Such changes in physical or chemical properties are then converted into a format easily read by an operator via electronic instruments, visually or physically detectable changes, or a combination of the two.

In another embodiment of the invention the nanostructured sensor is comprised of an array (ordered, partially-ordered or disordered) of zinc oxide nanostructures that change their physical or chemical properties including but not limited to optical, electrical properties, opto-electronic, piezoelectric, chemical or catalytic properties when it detects microbial organisms. Such changes in physical or chemical properties are then converted into a format easily read by an operator via electronic instruments, visually or physically detectable changes, or a combination of the two.

In another embodiment of the invention the nanostructured sensor is comprised of an array (ordered, partially-ordered or disordered) of zinc oxide nanorods that change their electrical properties such as electrical resistance when it detects microbial organisms. These changes are then converted into a format easily read by an operator via electronic instruments.

(III) Processes for Preparation of the Disclosure

The nanostructured sensors of the present disclosure may be prepared by techniques understood to those skilled in the art, and modified to expose the nanostructures during synthesis to a gravity field, a magnetic field, or both, the nanostructures being optionally aligned or anti-aligned with these fields. In one embodiment the exposed gravity fields can be modified by changing the alignment of the substrate relative to the gravity field. In another embodiment the magnetic fields can be introduced by placing a magnet under the synthetic apparatus or around the synthesis apparatus (to apply magnetic fields in different directions and with different controlled strengths). In a particular embodiment the nanostructures can be exposed to both the magnetic and gravity fields by placing a magnet underneath the substrate during synthesis while aligning the substrate with respect to the earth's gravitational field to achieve the desired gravitational field. In another embodiment a gravity field of desired strength can be induced by placing the synthetic apparatus within a centrifuge apparatus to achieve higher gravity fields among other techniques. In another embodiment the magnetic fields can be modified by placing the entire synthetic apparatus within a magnetic field of desired strength and homogeneity.

(IV) Uses of the Microbial Sensors

The microbial sensors of the present disclosure are useful in detection of microbes such as bacteria and fungi, and are designed to be operated by unskilled persons to detect the presence of bacterial contamination. As such these sensors can be incorporated into devices, systems or material packaging to indicate the presence of microbial contamination.

In a preferred embodiment such sensors can be incorporated into the inner packaging of various food products (animal and human), allowing the detection of microbial contamination within the packaged food. As zinc oxide is a known human dietary supplement and is non-toxic, such a sensor would pose no health related contamination issues to the packaged product.

In another embodiment such sensors can be used in grocery stores, restaurants, catering establishments, consumable food product storage facilities, as well as food and drink manufacturing facilities to test microbial contamination in the prepared foods.

In another embodiment such sensors can be used in general packaging and storage environments, where the presence of microbial contamination can result in product degradation, for example in wood based products, or products prone to decomposition under bacterial or fungal contamination.

In another embodiment such sensors can be used in hospitals, clinics, and other health and sanitary facilities, test for microbial contamination upon the premises.

(V) Examples

Example (I): Synthesis of ZnO Nanorods Under the Effects of Gravity and Magnetic Fields This synthesis is known as the original synthesis. In it Indium Tin Oxide (ITO) coated glass slides (ITO plates) were prepared with an initial cleaning of acetone in succession with ethanol and dried. A drop of zinc acetate dihydrate solution (0.005 M, in ethanol) was added to plate surface, then rinsed with clean ethanol and dried. This process was repeated a total of three times.

After initial preparation the ITO plates were heated in air for twenty minutes at either 300 or 350° C. The wetting process was once again performed, followed by twenty final minutes of heating, ensuring an even coverage. This annealing of the slide helps to ensure a stable fusion of the ZnO nanocrystals to the ITO plates. At this juncture, some ITO plates were suspended, with the Zn coated side face down so as to have nanostructure growth in the direction of the gravity field (with gravity), in a 90° C. solution of zinc nitrate hydrate (0.025 M) and hexamethylenetetramine (0.025 M) for two hours; Concurrently, other slides were allowed to rest on the bottom of the solution vessel, Zn coated side face up so as to have nanostructure growth against the direction of gravity (against gravity), and also allowed to react for two hours; The zinc nitrate hydrate and hexamethylenetetramine solution is heated and maintained at 90° C. using a hotplate with magnetic stirring, and thus possessed permanent magnets that simultaneously subjected both sets of ITO plates to the magnetic field of the permanent magnets and gravity (based on alignment of plates). After growth of the nanorods (2 hours in zinc nitrate hydrate solution) the ITO plates were washed with deionized water and dried. All samples were then prepared for scanning electron microscopy (SEM) and transmission electron microscopy (TEM) studies.

Figure 2:
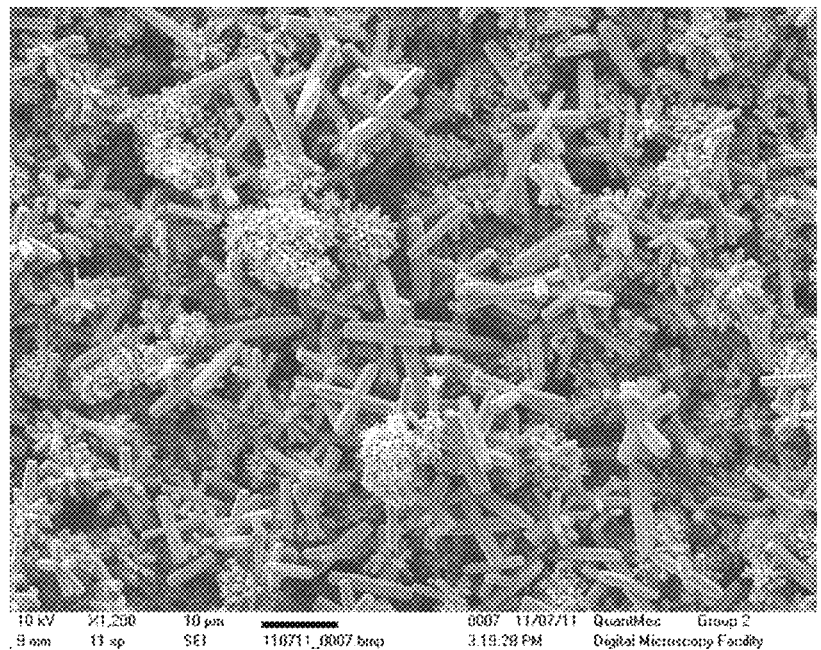
FIG. 2. SEM images of randomly oriented, "against gravity", ZnO nanoparticles shown with a 10 μm scale bar. Two distinct crystal morphologies are readily visible. Sample has an initial annealing temperature of 300° C.
Figure 3:
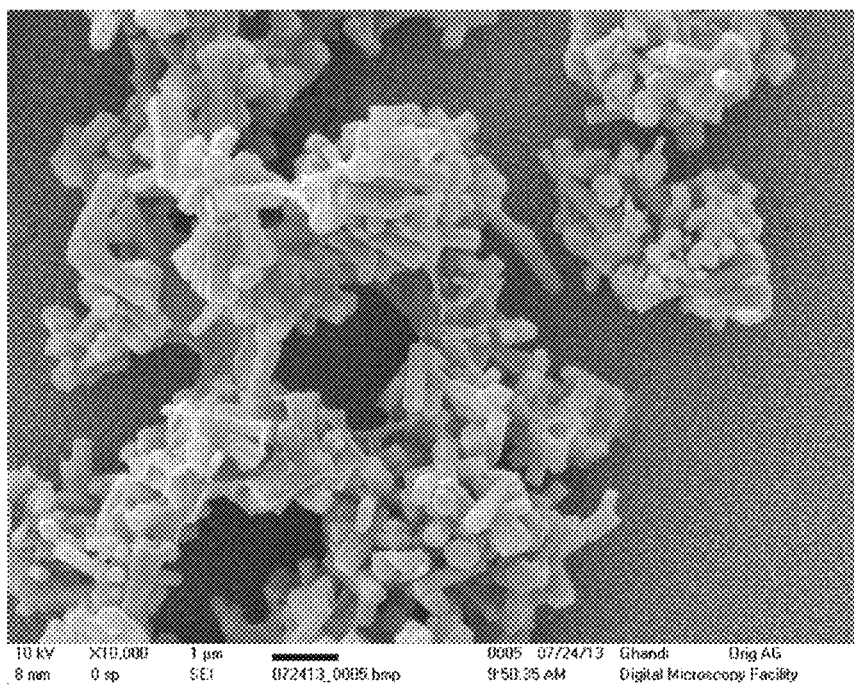
FIG. 3. SEM image of crystals grown against gravity under zero applied magnetic field, shown with a 1 μm scale bar.
Figure 4:
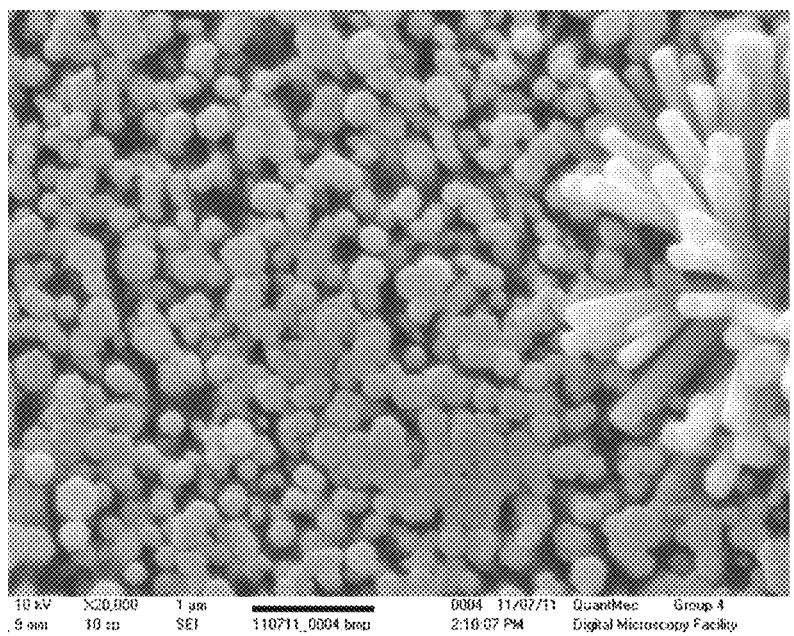
FIG. 4. SEM image of crystals grown with the influence of gravity under zero applied magnetic field, shown with a 1 μm scale bar.
Figure 5:
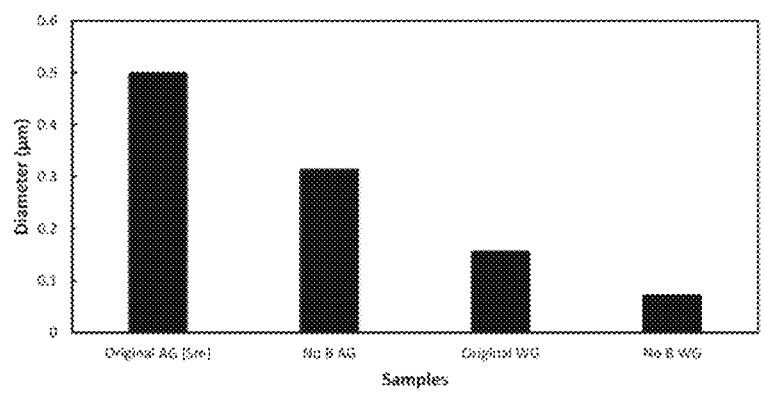
FIG. 5. Bar graph representing the diameter differences between the original sample and the no applied magnetic field sample. The abbreviations Original AG (Sm) represents the sample synthesized under conditions against the direction of gravity with the presence of a small magnetic field. No B AG represents the sample synthesized under conditions against the direction of gravity with no magnetic field present. Original WG represents the sample synthesized under conditions facing the direction of gravity with the presence of a small magnetic field. No B WG represents the sample synthesized under conditions facing the direction of gravity with no magnetic field present.
Figure 6:
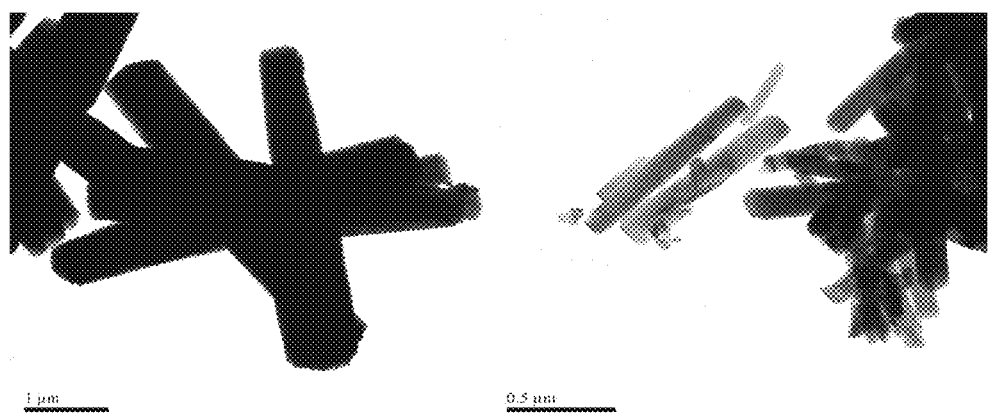
FIG. 6. Zinc Oxide nanorod images taken with transmission electron microscopy (TEM) using procedure from example I. Left: Against gravity. Right: Gravity assisted.

ZnO nanorods were synthesized in an effort to determine the effects of gravity on the growth process of crystal structures. It was observed through SEM and TEM (FIG. 6) that there is a pronounced effect on the structural morphology of the nanostructures that can be attributed to the effects of gravity and an applied magnetic field. FIG. 1 is an SEM image of the structural morphology of the ZnO nanorods grown with the influence of gravity, i.e. the ITO plate was suspended with the seeded side facing down; whereas FIG. 2 demonstrates the nanorods grown against the force of gravity. FIG. 1 shows a densely packed sheet of vertically aligned nanorods of rather uniform diameters (160±24 nm) with a few morphological defects, i.e. rods have merged into one mass. FIG. 2 demonstrates two distinct crystal growth morphologies, large hexagonal rods (often attached to form various structures) with average lengths and diameters of 9.2±1.9 µm and 1.8±0.5 µm respectively; in addition to small clusters of nanorod growth with average lengths and diameters of 1.9±0.5 µm and 0.5±0.1 µm respectively. The original synthesis was modified by influencing the growth of the aligned zinc nanorods with stronger magnetic fields. Magnetic field strengths and dimensions are presented in Table 1 as well as the comparison with the zero applied magnetic field.

TABLE 1

Growth dimension distributions influenced by changing magnetic field and alignment with gravity.

| β strength (gauss) | Growth with gravity | | Growth against gravity | |
|---|---|---|---|---|
| | Avg L (μm) | Avg Width (μm) | Avg Length (μm) | Avg Width (μm) |
| 0 | n/a | 0.16 ± 0.24 | 1.9 ± 0.5 | 0.5 ± 0.1 |
| 150 | 0.49 ± 0.14 | 0.14 ± 0.02 | 6.0 ± 1.9 | 0.65 ± 0.27 |
| 250 | 2.6 ± 0.7 | 0.56 ± 0.16 | 2.1 ± 0.2 | 0.73 ± 0.11 |
| 850 | 0.58 ± 0.13 | 0.14 ± 0.03 | 0.66 ± 0.11 | 0.17 ± 0.05 |

The difference between these structural morphologies is attributed to the effect of gravity and magnetic field. This effect may explain the deviant growth pattern towards alignment with the substrate; this however seems counter-intuitive as pure ZnO nanoparticles are diamagnetic. There is some indication however that when ZnO nanoparticles are capped with some organic surfactants the electronic structure is altered rendering them ferromagnetic-like.[12] Without being bound by theory, it is proposed that during the formation of the ZnO nanorods, the step in which the amine is interacting with the $Zn^{2+}$ species (see scheme 1) and subsequently with the hydroxyl group to form the final ZnO crystal, that the system may develop the aforementioned ferromagnetic-like properties. This effect on the intermediary step is what may cause the enhanced growth alignment with the applied magnetic field. Again, without being bound by theory, also included (see scheme 2) is a separate mechanism that may have a relationship to the synthesis in this example.[13]

Scheme 1. Chemical Reaction for the Formation of ZnO Nanostructures.

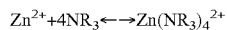

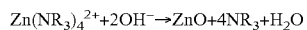

Scheme 2. Chemical Reaction for the Formation of ZnO Nanostructures Relating to Specific Synthesis Here-in Mentioned.

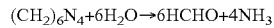

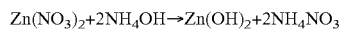

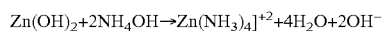

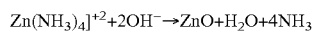

Example (II): Synthesis of Another Embodiment of ZnO Nanorods Under the Effects of Gravity Only The same procedure as Example I was followed for this example with the only difference being with regards to the hot plate used. In this example the zinc nitrate hydrate and hexamethylenetetramine solution is heated and maintained at 90° C. using a hotplate with no magnetic stirring functionality and thus no permanent magnets able to influence the growth process.

Figure 7:
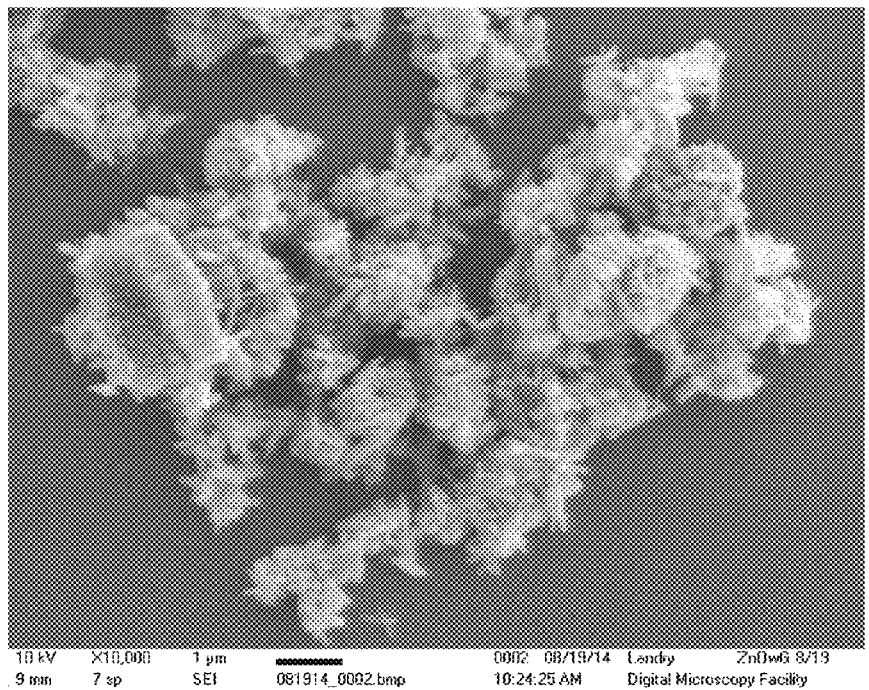
FIG. 7. Zinc Oxide nanorods grown with original synthesis against the influence of gravity in a 850 gauss magnetic field.
Figure 8:
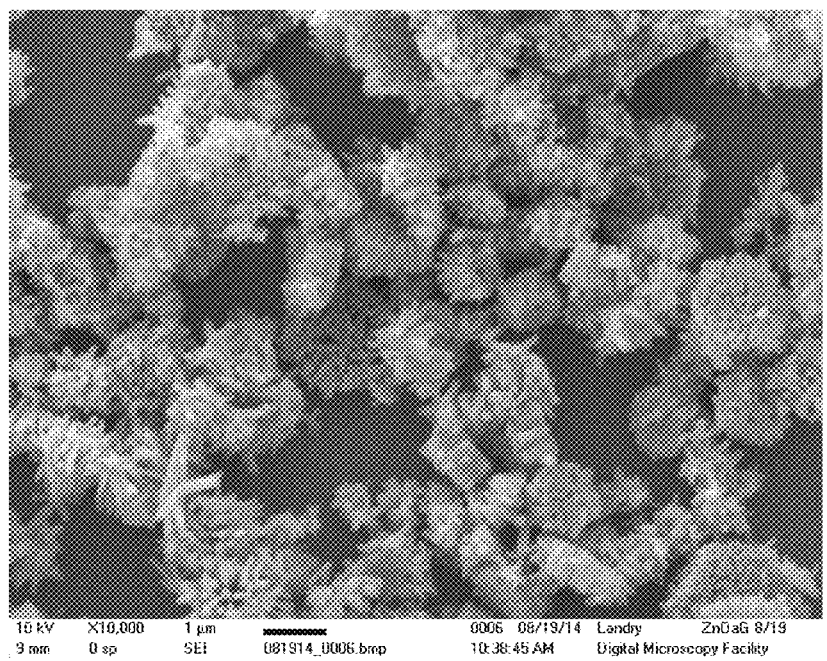
FIG. 8. Zinc Oxide nanorods grown with original synthesis with the influence of gravity in a 850 gauss magnetic field FIG. 9. Graph representing the change in the surface resistance of ZnO nanorod arrays when exposed to *ecoli* for a period of 48 hours. The ZnO nanorods are grown in alignment with the gravity field under the influence of a 250 gauss magnetic field. The results are an average of three replicates.

The effect of only the gravity field as compared to a combination of gravity and magnetic fields can be seen in comparing FIG. 1 to FIG. 4, it is readily apparent that in addition to the aligned rods (which are smaller in FIG. 4 than FIG. 1) there is an additional sheet-like structural morphology in certain combination of magnetic field structure and gravity. This effect is also seen in the experiment with no applied B, however there is only one growth morphology, indicating that the system is experiencing a similar environment across the sample while that in the presence of magnetic field experiences difference environments. Interestingly it seems that without the presence of a magnetic field, it is only the small crystal structures (approximately 1 μm in length) that are found. The "with gravity" samples of the original sample and the no applied field sample have average spacings of 87±32 nm and 54±13 nm respectively. Shown from the FIGS. 7 and 8, the application of strong magnetic fields results in the smallest dimensions of nanorods (refer to Table 1) from our series of synthesis for both with—and against—gravity and causes the ZnO nanorods to form bundles, aligning with other rods in the bundles, but not with other bundles. This is shown for both with—and against—gravity synthesis. Therefore the magnetic field has a strong effect on the alignment and growth of the nanorods.

It is demonstrated by these experiments that the morphology of the ZnO nanostructures is dependent both on the effects of gravitational forces and the presence of a magnetic field; and as such we have uncovered a valuable tool for the controlled synthesis of nanostructures.

Example (III): Synthesis of Another Embodiment of ZnO Nanorods Under the Effects of Gravity and Magnetic Fields Using Another Synthetic Technique ZnO nanorods were synthesized with the use of a stabilizing agent, ethanolamine. An initial solution of zinc acetate dihydrate (2.19 g), anhydrous ethanol (20 mL) and ethanolamine (6 M) was prepared and stirred at 60° C. for one hour with a hot plate capable of heating and magnetic stirring. This solution was allowed to stand for 24 hours for ageing. Soda-lime glass slides were washed with acetone and ethanol, dried, then dipped in the pre-made zinc acetate solution and allowed to dry. The coated glass slides were then placed on a hot plate at 500° C. to anneal for 1 hour; the dipping and annealing process was performed twice. After the annealing process the glass slides were placed in a 70° C. solution of zinc nitrate (0.03 g), sodium hydroxide (0.39 g) and deionized water (100 mL), as described above using a hot plate with both heating and magnetic stirring capabilities (exposure to a magnetic field). One of the glass slides was suspended while the other was allowed to rest on the bottom of the beaker. The slides remained in the solution for 1.5 hours before being removed and allowed to dry at room temperature.

Example (IV): Detection of Microbial Contamination by the Zinc Oxide Nanorod Array In our study, the zinc oxide sensors produced by Example 1 were studied for their ability to detect the bacteria *Bacillus cereus*, *Proteus hauseri*, *Proteus aeruginosa*, *Stapphylococcus aureus*, and *Escherichia coli*, and the fungi *saccharomyces cerevisiae*, *candida albicans*, and *aspergillus fumigatus*. Broth solutions of the bacteria and fungi in an exponential growth phase were individually spread onto nutrient agar plates. Mueller-Hinton nutrient agar was used for the bacteria and sabouraud nutrient agar for the fungi. The ZnO samples (nanorods grown on an ITO substrate as per Examples 1 and 2) were then placed onto on the agar and the plates were incubated at the optimum growth temperature of the respective bacteria and fungi for 24 hours. Afterward the samples were removed from the agar plates and the resistance of ZnO samples at a one centimeter distance between probes was measured. It is interesting to note that the resistance increased after test and that this increase varied with the difference bacterial and fungal organisms tested. A control group with just the ZnO sample with no bacteria or fungi in the agar plate is also incubated for 24 hours and then measured. The change in resistance upon detection of the bacteria is shown in Table 2, while the change in resistance upon detection of the various fungi is shown in Table 3.

TABLE 2

The measured electrical resistance of the zinc oxide sensors before and after bacterial tests

| | | Resistance/KΩ | | | | |
|---|---|---|---|---|---|---|
| Samples | Before Test | Bacillus Cereus | Proteus Aeruginosa | Proteus Hauseri, | Escherichia Coli | Control Group |
| ZnO WG | 3.19 ± 0.36 | 13.15 ± 0.49 | 153.33 ± 23.44 | 1910 ± 156 | 1579 ± 111 | 4.55 ± 2.03 |
| ZnO AG | 2.3 ± 1.7 | 220.07 ± 207.79 | 38.75 ± 15.48 | 5070 ± 2362 | 10.50 ± 6.79 | 0.85 ± 0.21 |

TABLE 3

The measured electrical resistance of the zinc oxide sensors before and after fungal tests

| | | Resistance/KΩ | | | |
|---|---|---|---|---|---|
| Samples | Before Test | Saccharomyces cerevisiae | Candida albicans | Aspergillus fumigatus | Control Group |
| ZnO WG | 65.4 ± 35.8 | 538 ± 54 | 13500 ± 707 | 86.15 ± 6.58 | 38.5 ± 9.19 |
| ZnO AG | 2.3 ± 1.7 | 30.067 ± 17.670 | 16.825 ± 5.056 | 4.39 ± 0.71 | 3.05 ± 0.92 |

Figure 9:
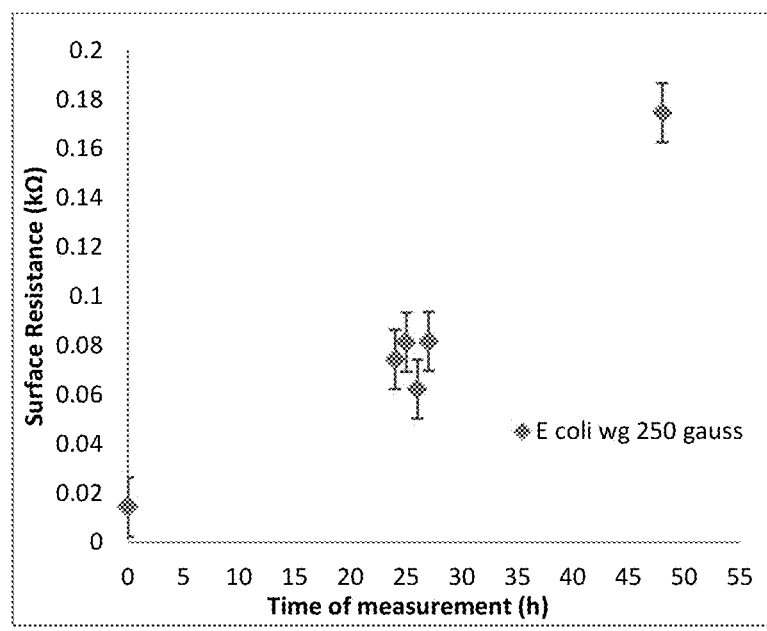

The resistance of the bacteria was also tested over a period of 48 hours at different time intervals (i.e. before introduction of bacteria, after 24 incubation period, at 25 hours, 26 hours, 27 hours, and at 48 hours where the bacteria was dead as determined by microscopic investigation). Results seen in FIG. 9 show resistance of the ZnO sample increases as *E. coli* growth covers the nanorods, and then increases once again as the bacteria die.

It can be seen that the described embodiments provide a unique and novel microbial sensor that has a number of advantages over those in the art. While there is shown and described herein certain specific structures embodying the invention, it will be manifest to those skilled in the art that various modifications and rearrangements may be made without departing from the spirit and scope of the underlying inventive concept and that the same is not limited to the particular forms herein shown and described except insofar as indicated by the scope of the appended claims.

REFERENCES (1) Tauxe, R.; Kruse, H.; Hedberg, C.; Potter, M.; Madden, J.; Wachsmuth, K. Microbial Hazards and Emerging Issues Associated with Produce: A Preliminary Report to the National Advisory Committee on Microbiologic Criteria for Foods. *Journal of Food Protection*, 60, 1400-1408.

(2) Wilcock, A.; Pun, M.; Khanona, J.; Aung, M. Consumer Attitudes, Knowledge and Behaviour: A Review of Food Safety Issues. *Trends Food Sci. Technol.* 2004, 15, 56-66.

(3) Alivisatos, P. The Use of Nanocrystals in Biological Detection. *Nat. Biotechnol.* 2004, 22, 47-52.

(4) Sanvicens, N.; Pastells, C.; Pascual, N.; Marco, M.-P. Nanoparticle-Based Biosensors for Detection of Pathogenic Bacteria. *TrAC Trends Anal. Chem.* 2009, 28, 1243-1252.

(5) Lim, C. T. Synthesis, Optical Properties, and Chemical-biological Sensing Applications of One-Dimensional Inorganic Semiconductor Nanowires. *Prog. Mater. Sci.* 2013, 58, 705-748.

(6) Barth, S.; Hernandez-Ramirez, F.; Holmes, J. D.; Romano-Rodriguez, A. Synthesis and Applications of One-Dimensional Semiconductors. *Prog. Mater. Sci.* 2010, 55, 563-627.

(7) Bancquart, S.; Vanhove, C.; Pouilloux, Y.; Barrault, J. Glycerol Transesterification with Methyl Stearate over Solid Basic Catalysts. *Appl. Catal. A Gen.* 2001, 218, 1-11.

(8) Liu, F.; Zhang, Y. Controllable Growth of "multi-Level Tower" ZnO for Biodiesel Production. *Ceram. Int* 2011, 37, 3193-3202.

(9) Zeng, J. H.; Jin, B. Bin; Wang, Y. F. Facet Enhanced Photocatalytic Effect with Uniform Single-Crystalline Zinc Oxide Nanodisks. *Chem. Phys. Lett.* 2009, 472, 90-95.

(10) Baruah, S.; Pal, S. K.; Dutta, J. Nanostructured Zinc Oxide for Water Treatment. *Nanosci. Nanotechnology-Asia* 2012, 2, 90-102.

(11) Lin, Y.-G.; Hsu, Y.-K.; Chen, S.-Y.; Lin, Y.-K.; Chen, L.-C.; Chen, K.-H. Nanostructured Zinc Oxide Nanorods with Copper Nanoparticles as a Microreformation Catalyst. *Angew. Chemie Int. Ed.* 2009, 48, 7586-7590.

(12) Garcia, M. a; Merino, J. M.; Fernández Pinel, E.; Quesada, a; de la Venta, J.; Ruíz González, M. L.; Castro, G. R.; Crespo, P.; Llopis, J.; González-Calbet, J. M.; et al. Magnetic Properties of ZnO Nanoparticles. *Nano Lett.* 2007, 7, 1489-1494.

(13) Baviskar, P. K.; Nikam, P. R.; Gargote, S. S.; Ennaoui, A.; Sankapal, B. R. Controlled Synthesis of ZnO Nanostructures with Assorted Morphologies via Simple Solution Chemistry. *J. Alloys Compd.* 2013, 551, 233-242.

What is claimed:

1. A sensor for detecting the presence of microbial organisms, comprising nanostructures or nanostructured materials incorporated in bulk materials; the nanostructures or nanostructured materials being free of any coatings of specific analytes, antibodies, ligands, receptors or chemical labels; and the nanostructures or nanostructured materials being capable of changing their physical or chemical properties upon detection of microbial organisms, wherein the nanostructures or nanostructured materials are configured to be synthesized under the simultaneous influence of gravity and magnetic fields, such that these fields influence the final shape and properties of the nanostructures or nanostructured materials.

2. A sensor according to claim 1, wherein the physical properties of the nanostructures or nanostructured materials that change upon bacterial detection include the materials optical, electrical properties, opto-electronic and piezoelectric properties or a combination thereof.

3. A sensor according to claim 1, wherein the chemical properties of the nanostructures or nanostructured materials that change upon bacterial detection include the materials catalytic properties or its chemical reactivity.

4. A sensor according to claim 1, wherein the sensor is comprised of an array of nanostructures that is optionally ordered, partially ordered, or completely disordered.

5. A sensor according to claim 1, wherein the change in physical or chemical properties of the nanostructure or nanostructured material upon detection of microbial organisms is translated into a format that may be understood by an operator using electronic instruments.

6. A sensor according to claim 1 wherein the change in physical or chemical properties of the nanostructure or nanostructured material upon detection of microbial organisms results in discernible changes in the optical properties of the sensor.

7. A sensor according to claim 1 wherein the nanostructures or nanostructured materials are optionally composed of one or more of the following components: metals, metal oxides, metal sulfides, doped metal sulfides, doped metal oxides, metal nitrides, doped metal nitrides, metal borides and di and tri borides (doped and undoped), metal selenides and doped metal selenides, Molybdenum disilicide, doped Molybdenum disilicide, carbon nanostructures, carbon nanotubes, and ceramic or polymeric materials.

8. A sensor according to claim 1 wherein the nanostructures or nanostructured materials are composed of nanostructures of zinc, copper, zinc oxide, zinc sulfide, zinc selenide, $RuO_2$, $IrO_2$, $CrO_2$, $ReO_3$, $TiN$, $TiB_2$, $MoSi_2$, and their doped states, and combinations thereof.

9. A sensor according to claim 1 wherein the nanostructures or nanostructured materials are composed of zinc oxide.

10. A sensor according to claim 9 wherein the nanostructures or nanostructured materials are rod-like structures.

11. A sensor according to claim 9 wherein the zinc oxide nanostructures or nanostructured materials substantially change their electrical resistance upon detection of microbial organisms.

12. A sensor according to claim 9, wherein the zinc oxide nanostructures or nanostructured materials substantially change their optical properties upon detection of microbial organisms.

13. A sensor according to claim 6 wherein the discernable changes to the optical properties upon microbial detection relate to the fluorescence wavelength, the fluorescence intensity, a combination of fluorescence wavelength and fluorescence intensity, or the optical absorption of the nanostructures.

14. A sensor according to claim 12 wherein the detection of microbial organisms results in a change in the sensor's fluorescence intensity, fluorescence wavelength, or both.

15. A sensor according to claim 1 wherein the sensor is incorporated into a food packaging material to detect the presence of microbial organisms within the package contents.

16. A sensor according to claim 1 wherein the sensor is incorporated into a consumable food product to detect the presence of microbial organisms within the product.

17. A sensor according to claim 1 wherein anti-microbial molecules are attached physically or chemically to the nanostructured sensors, allowing the sensor to both detect and kill microbial organisms that it contacts.

18. A sensor according to claim 1 wherein the nanostructured sensors are coated or grown onto a conductive, semiconductive, or non-conductive substrate.

19. A sensor according to claim 1 wherein the nanostructured sensors are coated onto an electronic screen, a window, a food preparation surface, a ventilation duct, a hygienic surface, or a combination thereof.

* * * * *